(12) United States Patent
Creech et al.

(10) Patent No.: US 6,933,147 B2
(45) Date of Patent: Aug. 23, 2005

(54) HUMAN CYCLIC NUCLEOTIDE-GATED CHANNEL POLYPEPTIDE

(75) Inventors: Christopher D. Creech, Garner, NC (US); Timothy J. Jegla, Durham, NC (US)

(73) Assignee: ICAgen, Inc., Durham, NC (US)

( * ) Notice: Subject to any disclaimer, the term of this patent is extended or adjusted under 35 U.S.C. 154(b) by 51 days.

(21) Appl. No.: 09/927,267

(22) Filed: Aug. 10, 2001

(65) Prior Publication Data

US 2002/0182691 A1 Dec. 5, 2002

Related U.S. Application Data

(60) Provisional application No. 60/226,253, filed on Aug. 17, 2000.

(51) Int. Cl.[7] .......................... C12N 15/85; C12N 1/21; C12N 1/15; C12N 15/63; C07H 21/04
(52) U.S. Cl. ............... 435/325; 435/252.3; 435/254.11; 435/254.2; 435/320.1; 536/23.5
(58) Field of Search ............................. 435/325, 252.3, 435/254.11, 254.2, 320.1; 536/23.5, 23.1, 24.3; 530/350

(56) References Cited

U.S. PATENT DOCUMENTS

2003/0013156 A1 * 1/2003 Guegler et al. ............ 435/69.1

FOREIGN PATENT DOCUMENTS

| WO | WO 01/81578 A2 | 11/2001 |
| WO | WO 02/02633 A3 | 1/2002 |
| WO | WO 02/02633 A2 | 1/2002 |

OTHER PUBLICATIONS

Birren et al, GenBank, Accession No. AC036216, May 4, 2000.*

Peer Bork and Eugene V. Koonin, Predicting functions from protein sequences—where are the bottlenecks? Nature Genetics 18:313–318, 1998.*

Ji et al. G–protein–coupled receptors, J. Biol. Chem., 273:17299–17302, 1998.*

Database EMBL Online. Jan. 24, 2000, Database Accession No. AC021935/XP002208958.

Database EMBL Online. Feb. 8, 2000, Database Accession No. AC022762.8/XP002208959.

Bradley, J. et al., "Heteromeric olfactory cyclic nucleotide-–gated channels: A subunit that confers increased sensitivity to cAMP," Proc. Natl. Acad. Sci. USA, Sep. 1994, pp. 8890–8894, vol. 91.

Ding, C. et al., "Cloning and widespread distribution of the rat rod–type cyclic nucleotide–gated cation channel," Am. J. Physiol., Apr. 1997, pp. C1335–C1344, vol. 272(4 part 1).

Finn, J. T. et al., "Cyclic nucleotide–gated ion channels: An extended family with diverse functions," Annu. Rev. Physiol., 1996, pp. 395–426, vol. 58.

Gerstner, A. et al., "Molecular cloning and functional characterization of a new modulatory cyclic nucleotide–gated channel subunit from mouse retina," Journal of Neuroscience, Feb. 15, 2000, pp. 1324–1332, vol. 20(4).

Kingston, P.A. et al., "Widespread expression of olfactory cyclic nucleotide–gated channel genes in rat brain: implications for neuronal signalling," Synapse, 1999, pp. 1–12, vol. 32.

Weyland, I. et al., "Cloning and functional expression of a cyclic–nucleotide–gated channel from mammalian sperm," Nature, Apr. 28, 1994, pp. 859–863, vol. 368(6474).

* cited by examiner

*Primary Examiner*—Ruixiang Li
(74) *Attorney, Agent, or Firm*—Townsend and Townsend and Crew, LLP

(57) ABSTRACT

The invention provides isolated nucleic acid and amino acid sequences of CNG2B, antibodies to CNG2B, methods of detecting CNG2B, and methods of screening for modulators of cyclic nucleotide-gated ion channels using biologically active CNG2B. The invention further provides, in a computer system, a method of screening for mutations of human CNG2B genes as well as a method for identifying a three-dimensional structure of human CNG2B polypeptides.

5 Claims, 4 Drawing Sheets

```
  1  MSQDTKVKTTESSPPAPSKARKLLPVLDPSGDYYYWWLNT    Cng2b.pro
  1  MSQDGKVKTTESTPPAPTKARKWLPVLDPSGDYYYWWLNT    rOCNC2.PRO 41  MVFPVMYNLIILVCRACFPDLQHGYLVAWLVLDYTSDLLY    Cng2b.pro
 41  MVFPIMYNLIIVVCRACFPDLQHSYLVAWFVLDYTSDLLY    rOCNC2.PRO 81  LLDMVVRFHTGFLEQGILVVDKGRISSRYVRTWSFLLDLA    Cng2b.pro
 81  LLDIGVRFHTGFLEQGILVVDKGMIASRYVRTWSFLLDLA    rOCNC2.PRO 121  SIMPTDVVYVRLGPHIPTLRLNRFLRAPRLFEAFDRTETR    Cng2b.pro
121  SLVPTDAAYVQLGPHIPTLRLNRFLRVPRLFEAFDRTETR    rOCNC2.PRO 161  TAYPNAFRIAKLMLYIFVVIHWNSCLYFALSRYLGFGRDA    Cng2b.pro
161  TAYPNAFRIAKLMLYIFVVIHWNSCLYFALSRYLGFGRDA    rOCNC2.PRO 201  WVYPDPAQPGFERLRRQYLYSFYFSTLILTTVGDTPPPAR    Cng2b.pro
201  WVYPDPAQPGFERLRRQYLYSFYFSTLILTTVGDTPPPDR    rOCNC2.PRO 241  EEEYLFMVGDFLLAVMGFATIMGSMSSVIYNMNTADAAFY    Cng2b.pro
241  EEEYLFMVGDFLLAVMGFATIMGSMSSVIYNMNTADAAFY    rOCNC2.PRO 281  PDHALVKKYMKLQHVNRKLERRVIDWYQHLQINKKMTNEV    Cng2b.pro
281  PDHALVKKYMKLQHVNKRLERRVIDWYQHLQINKKMTNEV    rOCNC2.PRO 321  AILQHLPERLRAEVAVSVHLSTLSRVQIFQNCEASLLEEL    Cng2b.pro
321  AILQHLPERLRAEVAVSVHLSTLSRVQIFQNCEASLLEEL    rOCNC2.PRO 361  VLKLQPQTYSPGEYVCRKGDIGQEMYIIREGQLAVVADDG    Cng2b.pro
361  VLKLQPQTYSPGEYVCRKGDIGREMYIIREGQLAVVADDG    rOCNC2.PRO 401  ITQYAVLGAGLYFGEISIINIKGNMSGNRRTANIKSLGYS    Cng2b.pro
401  VTQYAVLGAGLYFGEISIINIKGNMSGNRRTANIKSLGYS    rOCNC2.PRO 441  DLFCLSKEDLREVLSEYPQAQTIMEEKGREILLKMNKLDV    Cng2b.pro
441  DLFCLSKEDLREVLSEYPQAQAVMEEKGREILLKMNKLDV    rOCNC2.PRO 481  NAEAAEIALQEATESRLRGLDQQLDDLQTKFARLLAELES    Cng2.pro
481  NAEAAEIALQEATESRLKGLDQQLDDLQTKFARLLAELES    rOCNC2.PRO 521  SALKIAVRIERLEWQTREWPMPEDIAEADDEGEPEEGTSK    Cng2.pro
521  SALKIAVRIERLEWQTREWPMPEDMGEADDEAEPGEGTSK    rOCNC2.PRO 561  DEEGRASQEGPEGEE                             Cng2.pro
561  DGEGKAGQAGPSGIE                             rOCNC2.PRO
```

FIG. 1.

```
AGAGGGGAGGAGGAAAACAGAGACAAGACTCAGGCTTCCCTCTGAGGCATGCACCCC
CACCTTCTCCAGGGATCTCATTAGAGGTGTTTAGCTGGGCAGGTGTAAGCCCAGGCC
CTGGGAGACAGGGCAGAGTGCTAGAGCTAGACTGTCTCCACCCCTTCAGTAGCGCTA
GCTCTGGTTGTGTTGCTAAGAGCCCCAAAGACAAAGAAGTCACAGCAGAAGCCCAAC
AGCAGCCTCCTTCAGACAGTCAGGCACTAGTGCCCAACTCCAGAAGTCCCCTACAGG
CAGAGAGGGTGTGGACATCTCACACCCCAGCACCAGACCACAGAACCATGAGCCAGG
ACACCAAAGTGAAGACAACAGAGTCCAGTCCCCAGCCCCATCCAAGGCCAGGAAGT
TGCTGCCTGTCCTGGACCCATCTGGGGATTACTACTACTGGTGGCTGAACACAATGG
TCTTCCCAGTCATGTATAACCTCATCATCCTCGTGTGCAGAGCCTGCTTCCCCGACT
TGCAGCACGGTTATCTGGTGGCCTGGTTGGTGCTGGACTACACGAGTGACCTGCTAT
ACCTACTAGACATGGTGGTGCGCTTCCACACAGGATTCTTGGAACAGGGCATCCTGG
TGGTGGACAAGGGTAGGATCTCGAGTCGCTACGTTCGCACCTGGAGTTTCTTCTTGG
ACCTGGCTTCCCTGATGCCCACAGATGTGGTCTACGTGCGGCTGGGCCCGCACACAC
CCACCCTGAGGCTGAACCGCTTTCTCCGCGCGCCCCGCCTCTTCGAGGCCTTCGACC
GCACAGAGACCCGCACAGCTTACCCAAATGCCTTTCGCATTGCCAAGCTGATGCTTT
ACATTTTTGTCGTCATCCATTGGAACAGCTGCCTATACTTTGCCCTATCCCGGTACC
TGGGCTTCGGGCGTGACGCATGGGTGTACCCGGACCCCGCGCAGCCTGGCTTTGAGC
GCCTGCGGCGCCAGTACCTCTATAGCTTTTACTTCTCCACGCTGATACTGACTACAG
TGGGCGATACACCGCCGCCAGCCAGGGAAGAAGAGTACCTCTTCATGGTGGGCGACT
TCCTGCTGGCCGTCATGGGTTTCGCCACCATCATGGGTAGCATGAGCTCTGTCATCT
ACAACATGAACACTGCAGATGCGGCTTTCTACCCAGATCATGCACTGGTGAAGAAGT
ACATGAAGCTGCAGCACGTCAACCGCAAGCTGGAGCGGCGAGTTATTGACTGGTATC
AGCACCTGCAGATCAACAAGAAGATGACCAACGAGGTAGCCATCTTACAGCACTTGC
CTGAGCGGCTGCGGGCAGAAGTGGCTGTGTCTGTGCACCTGTCCACTCTGAGCCGGG
TGCAGATCTTTCAGAACTGTGAGGCCAGCCTGCTGGAGGAGCTGGTGCTGAAGCTGC
AGCCCCAGACCTACTCACCAGGTGAATATGTATGCCGCAAAGGAGACATTGGCCAAG
AGATGTACATCATCCGAGAGGGTCAACTGGCCGTGGTGGCAGATGATGGTATCACAC
AGTAGCTGTGCTCGGTGCAGGGCTCTACTTTGGGGAGATCAGCATCATCAACATCAA
AGGGAACATGTCTGGGAACCGCCGCACAGCCAACATCAAGAGCCTAGGTTATTCAGA
CCTATTCTGCCTGAGCAAGGAGGACCTGCGGGAGGTGCTGAGCGAGTATCCACAAGC
ACAGACCATCATGGAGGAGAAGGACGTGAGATCCTGCTGAAAATGAACAAGTTGGA
CGTGAATGCTGAGGCAGCTGAGATCGCCCTGCAGGAGGCCACAGAGTCCCGGCTACG
AGGCCTAGACCAGCAGCTGGATGATCTACAGACCAAGTTTGCTCGCCTCCTGGCTGA
GCTGGAGTCCAGCGCACTTAAGATTGCTTACCGCATTGAACGGCTGGAGTGGCAGAC
TCGAGAGTGGCCAATGCCCGAGGACCTGGCTGAGGCTGATGACGAGGGTGAGCCTGA
GGAGGGAACTTCCAAAGATGAAGAGGGCAGGGCCAGCCAGGAGGGACCCCCAGGTCC
AGAGTGACCCCATCCCCATCCCCAGGATTCCCACCTCCTAGTGAATCCAGAGTTGTA
GTAAAGCCTAACTGCTGCAACTCTGTCATCCTGTCTGCGAGATCACAGACACAGGAG
CGAATTGGTCTGTAGATGCCCAGCTAGAGATATAGGAGTTTAACGCACATTCAGCCC
CCACTTACCAGTACACACACACACACACACACACACATTTGCTCATAGACCTGTT
GGCCCCAAGACTGTGCATTCCATCTAA
```

FIG. 2.

```
ATGAGCCAGGACACCAAAGTGAAGACAACAGAGTCCAGTCCCCCAGCCCCATCCAAG
GCCAGGAAGTTGCTGCCTGTCCTGGACCCATCTGGGGATTACTACTACTGGTGGCTG
AACACAATGGTCTTCCCAGTCATGTATAACCTCATCATCCTCGTGTGCAGAGCCTGC
TTCCCCGACTTGCAGCACGGTTATCTGGTGGCCTGGTTGGTGCTGGACTACACGAGT
GACCTGCTATACCTACTAGACATGGTGGTGCGCTTCCACACAGGATTCTTGGAACAG
GGCATCCTGGTGGTGGACAAGGGTAGGATCTCGAGTCGCTACGTTCGCACCTGGAGT
TTCTTCTTGGACCTGGCTTCCCTGATGCCCACAGATGTGGTCTACGTGCGGCTGGGC
CCGCACACACCCACCCTGAGGCTGAACCGCTTTCTCCGCGCGCCCCGCCTCTTCGAG
GCCTTCGACCGCACAGAGACCCGCACAGCTTACCCAAATGCCTTTCGCATTGCCAAG
CTGATGCTTTACATTTTTGTCGTCATCCATTGGAACAGCTGCCTATACTTTGCCCTA
TCCCGGTACCTGGGCTTCGGGCGTGACGCATGGGTGTACCCGGACCCCGCGCAGCCT
GGCTTTGAGCGCCTGCGGCGCCAGTACCTCTATAGCTTTTACTTCTCCACGCTGATA
CTGACTACAGTGGGCGATACACCGCCGCCAGCCAGGGAAGAAGAGTACCTCTTCATG
GTGGGCGACTTCCTGCTGGCCGTCATGGGTTTCGCCACCATCATGGGTAGCATGAGC
TCTGTCATCTACAACATGAACACTGCAGATGCGGCTTTCTACCCAGATCATGCACTG
GTGAAGAAGTACATGAAGCTGCAGCACGTCAACCGCAAGCTGGAGCGGCGAGTTATT
GACTGGTATCAGCACCTGCAGATCAACAAGAAGATGACCAACGAGGTAGCCATCTTA
CAGCACTTGCCTGAGCGGCTGCGGGCAGAAGTGGCTGTGTCTGTGCACCTGTCCACT
CTGAGCCGGGTGCAGATCTTTCAGAACTGTGAGGCCAGCCTGCTGGAGGAGCTGGTG
CTGAAGCTGCAGCCCCAGACCTACTCACCAGGTGAATATGTATGCCGCAAAGGAGAC
ATTGGCCAAGAGATGTACATCATCCGAGAGGGTCAACTGGCCGTGGTGGCAGATGAT
GGTATCACACAGTATGCTGTGCTCGGTGCAGGGCTCTACTTTGGGGAGATCAGCATC
ATCAACATCAAAGGGAACATGTCTGGGAACCGCCGCACAGCCAACATCAAGAGCCTA
GGTTATTCAGACCTATTCTGCCTGAGCAAGGAGGACCTGCGGGAGGTGCTGAGCGAG
TATCCACAAGCACAGACCATCATGGAGGAGAAGGACGTGAGATCCTGCTGAAAATG
AACAAGTTGGACGTGAATGCTGAGGCAGCTGAGATCGCCCTGCAGGAGGCCACAGAG
TCCCGGCTACGAGGCCTAGACCAGCAGCTGGATGATCTACAGACCAAGTTTGCTCGC
CTCCTGGCTGAGCTGGAGTCCAGCGCACTTAAGATTGCTTACCGCATTGAACGGCTG
GAGTGGCAGACTCGAGAGTGGCCAATGCCCGAGGACCTGGCTGAGGCTGATGACGAG
GGTGAGCCTGAGGAGGGAACTTCCAAAGATGAAGAGGGCAGGGCCAGCCAGGAGGGA
CCCCCAGGTCCAGAGTGA
```

*FIG. 3.*

MSQDTKVKTTESSPPAPSKARKLLPVLDPSGDYYYWWLNTMVFPVMYNLIILVCRAC
FPDLQHGYLVAWLVLDYTSDLLYLLDMVVRFHTGFLEQGILVVDKGRISSRYVRTWS
FFLDLASLMPTDVVYVRLGPHTPTLRLNRFLRAPRLFEAFDRTETRTAYPNAFRIAK
LMLYIFVVIHWNSCLYFALSRYLGFGRDAWVYPDPAQPGFERLRRQYLYSFYFSTLI
LTTVGDTPPPAREEEYLFMVGDFLLAVMGFATIMGSMSSVIYNMNTADAAFYPDHAL
VKKYMKLQHVNRKLERRVIDWYQHLQINKKMTNEVAILQHLPERLRAEVAVSVHLST
LSRVQIFQNCEASLLEELVLKLQPQTYSPGEYVCRKGDIGQEMYIIREGQLAVVADD
GITQYAVLGAGLYFGEISIINIKGNMSGNRRTANIKSLGYSDLFCLSKEDLREVLSE
YPQAQTIMEEKGREILLKMNKLDVNAEAAEIALQEATESRLRGLDQQLDDLQTKFAR
LLAELESSALKIAYRIERLEWQTREWPMPEDLAEADDEGEPEEGTSKDEEGRASQEG
PPGPE

FIG. 4.

HUMAN CYCLIC NUCLEOTIDE-GATED CHANNEL POLYPEPTIDE

CROSS-REFERENCES TO RELATED APPLICATIONS

The present application claims priority to U.S. Ser. No. 60/226,253, filed Aug. 17, 2000, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The invention provides isolated nucleic acid and amino acid sequences of CNG2B, antibodies to CNG2B, methods of detecting CNG2B, and methods of screening for modulators of cyclic nucleotide-gated cation channels using biologically active CNG2B. The invention further provides, in a computer system, a method of screening for mutations of human CNG2B genes as well as a method for identifying a three-dimensional structure of human CNG2B polypeptides.

BACKGROUND OF THE INVENTION

Cyclic nucleotide gated cation channels (CNG) are a class of non-selective cation channels that are opened by direct binding of cyclic nucleotides such as cGMP and cAMP. CNG channels are highly permeable to $Na^+$ and $Ca^{2+}$ and their activation leads to depolarization and increases in internal $Ca^{2+}$ concentrations. These channels can link changes in cytoplasmic cyclic nucleotide levels to changes in cellular excitability, secretion of neurotransmitters and the stimulation of calcium-dependent pathways.

CNG family channel proteins are multimers and can be formed by at least two functionally distinct classes of subunits. The two classes of subunits, alpha and beta, share a common motif of 6 transmembrane domains, a pore motif and a cytoplasmic cyclic nucleotide binding domain (Finn et al., *Annu. Rev. Physiol.* 58:395–426:1996). CNG alpha subunits can form functional channels as homomultimers, i.e., all subunits contributing to the channel pore are identical. Beta subunits, in contrast, can only form functional channels when expressed with an alpha subunit. These heteromultimeric channels show functional properties consistent with native CNG channels (Gerstner, et al., *J. Neurosci.* 20(4):1324–1332, 2000; Finn, et al., *Annu. Rev. Physiol.* 58:395–426, 1996). For example, coexpression of alpha and beta subunits occurs in retinal rod cells where the alpha subunit CNGA1 forms a heteromultimer with the beta subunit CNGB1 (CNG4) (Gerstner, et al, *J. Neurosci.* 20(4): 1324–1332, Feb. 15, 2000).

CNG channels are important for sensory signal transduction in retinal and olfactory and taste bud cells in response to primary sensory stimuli such as light and aerosolized or dissolved molecules (Ding, C, et al., *Am. J. Physiol.* 272 (*Cell Physiol.* 41): C1335–C1344, 1997). In photoreceptor cells, CNG channels are open in darkness due to a high basal concentration of cGMP. This causes a tonic depolarization of the membrane and constitutive neurotransmitter release. Upon stimulation by light, cGMP levels drop, closing the CNG channels. This in turn causes a hyperpolarization of the membrane, a drop in the internal $Ca^{2+}$ concentration, and a decrease in the release of neurotransmitter (Finn, et al., *Annu. Rev. Physiol.* 58:395–426, 1996).

CNG channels have been found in a number of tissues, suggesting that these channels may link a variety of stimuli to changes in membrane potential and cytoplasmic calcium levels (Ding, et al., *Am. J. Physiol.* 272 (*Cell Physiol.* 41):C1335–C1344, 1997; Kingston P, *Synapse* 32:1–12, 1999). For instance, retinal and olfactory CNG channels are expressed in various parts of the brain (Ding, et al, *Am. J. Physiol.* 272 (*Cell Physiol.* 41):C1335–C1344, 1997; Kingston P, *Synapse* 32:1–12, 1999). Because these channels are highly permeable to $Ca^{2+}$, they may stimulate $Ca^{2+}$-dependent pathways that have significant effects on neuronal activity. More directly, they may contribute to neuronal activity by providing excitatory depolarizations. CNG channels may also interact with other second messenger systems such as the Nitric Oxide-pathway to provide the longer lasting changes that are important mechanisms in learning and memory (Kingston, *Synapse* 32:1–12, 1999). CNG channels have been found in the testis, and through the regulation of the internal $Ca^{2+}$ concentration, may be involved in chemotaxis of sperm (Weyand, et al., *Nature* 368:859–863, 1994). Expression of CNG channels has also been noted in heart, aorta and kidney, where they may play a role in the regulation of heart rate, blood pressure and electrolyte transport, respectively (Finn et al., *Ann. Rev. Physiol.* 1996, 58:395–426). The full scope of CNG channel function is not yet entirely understood, but it is clear that they play a key role in many physiological processes.

SUMMARY OF THE INVENTION

The current invention provides the first isolation and characterization of human CNG2B, a novel subunit of a cyclic nucleotide gated cation channel. The present invention provides both the nucleotide and amino acid sequence of CNG2B, as well as methods of assaying for modulators of CNG2B, antibodies to CNG2B, and methods of detecting CNG2B nucleic acids and proteins.

In one aspect, the present invention provides an isolated nucleic acid encoding a polypeptide comprising a subunit of a cation channel, the polypeptide: (i) forming, with at least one CNG alpha subunit, a cation channel having the characteristic of cyclic nucleotide-gating or nitric oxide gating; and (ii) comprising an amino acid sequence having at least 95% identity to SEQ ID NO:1.

In another aspect, the present invention provides an isolated nucleic acid encoding a CNG2B polypeptide, the nucleic acid specifically hybridizing under stringent conditions to a nucleic acid comprising a nucleotide sequence of SEQ ID NO:2 or SEQ ID NO:3.

In another aspect, the present invention provides an isolated nucleic acid encoding a CNG2B polypeptide, the nucleic acid comprising a nucleotide sequence having at least 90% sequence identity to SEQ ID NO:2 or SEQ ID NO:3.

In one embodiment, the nucleic acid encodes a polypeptide comprising an amino acid sequence of SEQ ID NO:1. In another embodiment, the nucleic acid comprises a nucleotide sequence of SEQ ID NO:2 or SEQ ID NO:3.

In another embodiment, the nucleic acid is amplified by primers that selectively hybridize under stringent hybridization conditions to the same sequence as the primers selected from the group consisting of:

| | |
|---|---|
| GCAGATCTTTCAGAACTGTGAGGCCA | (SEQ ID NO:4) |
| CCTGCCCTCTTCATCTTTGGAAGTTC | (SEQ ID NO:5) |
| GCCAACATCAAGAGCCTAGGTTATTC | (SEQ ID NO:6) |
| GGATGATCTACAGACCAAGTTTGCTCG | (SEQ ID NO:7) |
| ATGAGCCAGGACACCAAAGTGAAGAC | (SEQ ID NO:8) |
| GTTGATGATGCTGATCTCCCCAAAG | (SEQ ID NO:9) |
| GGATGATGAGGTTATACATGACTGGG | (SEQ ID NO:10) |
| AGGCTAGCAACTTCCTGGCCTTGGAT | (SEQ ID NO:11) |
| GCGAAAGCTTCCACCATGAGCCAGGACACCA AAGTG | (SEQ ID NO:12) and |
| CATGTCTAGAATGGGGATGGGGTCACTCTGG ACCT | (SEQ ID NO:13). |

In another embodiment, the nucleic acid selectively hybridizes under moderately stringent hybridization conditions to a nucleic acid comprising a nucleotide sequence of SEQ ID NO:2 or SEQ ID NO:3. In another aspect, the present invention provides an isolated nucleic acid that specifically hybridizes under stringent conditions to a nucleic acid encoding an amino acid sequence of SEQ ID NO:1.

In another aspect, the present invention provides a method of detecting a nucleic acid, the method comprising contacting the nucleic acid with an isolated nucleic acid, as described above.

In another aspect, the present invention provides expression vectors comprising the nucleic acids of the invention, and host cells comprising such expression vectors.

In another aspect, the present invention provides an isolated polypeptide comprising a subunit of a cation channel, the polypeptide: (i) forming, with at least one CNG alpha subunit, a cation channel having the characteristic of cyclic nucleotide-gating; and (ii) comprising an amino acid sequence having at least 95% sequence identity to SEQ ID NO:1.

In one embodiment, the polypeptide specifically binds to antibodies generated against a polypeptide comprising an amino acid sequence of SEQ ID NO:1. In another embodiment, the polypeptide comprises an alpha subunit of a homomeric cyclic nucleotide gated cation channel. In another embodiment, the polypeptide comprises an alpha subunit of a heteromeric cyclic nucleotide gated cation channel. In another embodiment, the polypeptide has a molecular weight of between about 61 kD to about 71 kD. In another embodiment, the polypeptide has an amino acid sequence of human CNG2B. In another embodiment, the polypeptide has an amino acid sequence of SEQ ID NO:1.

In another aspect, the present invention provides an antibody that specifically binds to any of the CNG2B polypeptides described herein.

In another aspect, the present invention provides a method for identifying a compound that increases or decreases ion flux through a cation channel, the method comprising the steps of: (i) contacting the compound with a CNG2B polypeptide, the polypeptide (a) forming, with at least one CNG alpha subunit, a cation channel having the characteristic of cyclic nucleotide-gating; and (b) comprising an amino acid sequence having at least 95% sequence identity to SEQ ID NO:1; and (ii) determining the functional effect of the compound upon the cation channel.

In one embodiment, the functional effect is a physical effect or a chemical effect. In one embodiment, the polypeptide is recombinant. In another embodiment, the functional effect is determined by measuring ligand binding to the channel. In another embodiment, the cation channel is homomultimeric. In another embodiment, the cation channel is heteromultimeric.

In one embodiment, the polypeptide is expressed in a eukaryotic host cell or cell membrane. In another embodiment, the functional effect is determined by measuring ion flux, changes in ion concentrations, changes in current or changes in voltage.

In another aspect, the present invention provides a method for identifying a compound that increases or decreases ion flux through a cyclic nucleotide-gated cation channel comprising a CNG2B polypeptide, the method comprising the steps of: (i) entering into a computer system an amino acid sequence of at least 100 amino acids of a CNG2B polypeptide or at least 300 nucleotides of a nucleic acid encoding the CNG2B polypeptide, the CNG2B polypeptide comprising an amino acid sequence having at least 95% sequence identity to SEQ ID NO:1; (ii) generating a three-dimensional structure of the polypeptide encoded by the amino acid sequence; (iii) generating a three-dimensional structure of the cation channel comprising the CNG2B polypeptide; (iv) generating a three-dimensional structure of the compound; and (v) comparing the three-dimensional structures of the polypeptide and the compound to determine whether or not the compound binds to the polypeptide.

In one embodiment, the amino acid sequence is of a full-length CNG2B polypeptide.

In another aspect, the present invention provides a method of modulating ion flux through a CNG cation channel comprising a CNG2B subunit to treat a disease in a subject, the method comprising the step of administering to the subject a therapeutically effective amount of a compound identified using any of the methods described herein.

In another aspect, the present invention provides a method of detecting the presence of CNG2B in human tissue, the method comprising the steps of: (i) isolating a biological sample; (ii) contacting the biological sample with an CNG2B-specific reagent that selectively associates with CNG2B; and, (iii) detecting the level of CNG2B-specific reagent that selectively associates with the sample.

In one embodiment, the CNG2B-specific reagent is selected from the group consisting of: CNG2B-specific antibodies, CNG2B-specific oligonucleotide primers, and CNG2B-nucleic acid probes.

In another aspect, the present invention provides, in a computer system, a method of screening for mutations of a human CNG2B gene, the method comprising the steps of: (i) entering into the computer a first nucleic acid sequence encoding a CNG2B polypeptide having a nucleotide sequence of, SEQ ID NO:2 or SEQ ID NO:3, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

BRIEF DESCRIPTION OF THE DRAWINGS

FIG. 1. Amino acid alignment of CNG2B (SEQ ID NO:1) with rat OCNC2 (SEQ ID NO:16). Identical residues are shaded and numbers at the left margin indicate amino acid position.

FIG. 2. Complete CNG2B sequence derived from assembly of PCR fragments (SEQ ID NO:2).

FIG. 3. Complete CNG2B coding nucleotide sequence (SEQ ID NO:3).

FIG. 4. Complete CNG2B amino acid sequence (SEQ ID NO1).

DETAILED DESCRIPTION OF THE INVENTION

I. Introduction

The present invention provides for the first time nucleic acids encoding CNG2B, a member of the CNG family of cyclic nucleotide gated cation channels. Members of this family are polypeptide subunits of cation channels having six transmembrane regions, a pore motif, and a cytoplasmic cyclic nucleotide binding domain. CNG2B is most similar to rat OCNC2 which, without being bound to any particular theory, has characteristics of both alpha and beta subunits. Because CNG2B is expressed in the central nervous system, modulators of CNG2B function can be identified which would be useful in the treatment of any of a large number of neurological disorders.

The invention therefore provides methods of screening for activators and inhibitors of cation channels that contain a CNG2B subunit. Such modulators of cation channel activity are useful for treating disorders, including neurological disorders.

Furthermore, the invention provides assays for CNG activity where CNG2B acts as a direct or indirect reporter molecule. Such uses of CNG2B as a reporter molecule in assay and detection systems have broad applications, e.g., CNG2B can be used as a reporter molecule to measure changes in cation concentration, membrane potential, current flow, ion flux, transcription, signal transduction, receptor-ligand interactions, second messenger concentrations, in vitro, in vivo, and ex vivo. In one embodiment, CNG2B can be used as an indicator of current flow in a particular direction (e.g., outward or inward cation flow), and in another embodiment, CNG2B can be used as an indirect reporter via attachment to a second reporter molecule such as green fluorescent protein.

The invention also provides for methods of detecting CNG2B nucleic acid and protein expression, allowing investigation of the channel diversity provided by CNG2B family members, as well as diagnosis of disorders, including neurological disorders.

Finally, the invention provides for a method of screening for mutations of CNG2B genes or proteins. The invention includes, but is not limited to, methods of screening for mutations in CNG2B with the use of a computer. Similarly, the invention provides for methods of identifying the three-dimensional structure of CNG2B polypeptides, as well as the resulting computer readable images or data that comprise the three dimensional structure of CNG2B polypeptides. Other methods for screening for mutations of CNG2B genes or proteins include high density oligonucleotide arrays, PCR, immunoassays and the like.

Functionally, CNG2B polypeptides are subunits, e.g., alpha subunits, of cyclic nucleotide-gated cation channels. CNG2B-containing channels are either homomultimeric or heteromultimeric. Heteromultimeric CNG2B-containing channels can contain, in addition to the CNG2B subunits, one or more CNG alpha or beta subunits. The presence of CNG2B in a cation channel may modulate the activity of the heteromeric channel and thus enhance channel diversity. Channel diversity is also enhanced with alternatively spliced forms of CNG2B genes. CNG2B nucleic acids have been isolated from cDNAs from the human central nervous system.

Structurally, the nucleotide sequence of human CNG2B (SEQ ID NOS:2–3) encodes a polypeptide monomer with a predicted molecular weight of approximately 66 kD and a predicted molecular weight range of 61–71 kD. CNG2B polypeptides typically contain each of the motifs common among alpha and beta CNG subunits, including six transmembrane domains, a pore motif, and a cytoplasmic cyclic nucleotide binding domain (Finn et al., Ann. Rev. Physiol. 58:395–426:1996). Related CNG2B genes from other species share at least about 60%, 65%, 70%, 75%, 80%, 85%, 90% or, preferably, 95% to 100% amino acid identity with the CNG2B shown as SEQ ID NO:1.

The present invention also provides polymorphic variants of the human CNG2B depicted in SEQ ID NO:1: variant #1, in which an isoleucine residue is substituted for the valine residue at amino acid position 110; variant #2, in which a glycine residue is substituted for the serine residue at amino acid position 520; variant #3, in which a lysine residue is substituted for the arginine residue at amino acid position 537; and variant #4, in which a glutamic acid residue is substituted for the aspartic acid residue at amino acid position 550.

The CNG2B nucleotide and amino acid sequence may be used to identify CNG2B polymorphic variants, interspecies homologs, and alleles. This identification can be made in vitro, e.g., under stringent hybridization conditions and sequencing, or by using the sequence information in a computer system for comparison with other nucleotide sequences, or using antibodies raised against CNG2B. Typically, identification of CNG2B polymorphic variants, orthologs, and alleles is made by comparing the amino acid sequence (or the nucleic acid encoding the amino acid sequence) of SEQ ID NO:1. Amino acid identity of approximately at least 60% or above, 70%, 65%, 75%, 80%, preferably 85%, most preferably 95%, 96%, 97%, 98%, or 99% typically demonstrates that a protein is a CNG2B polymorphic variant, interspecies homolog, or allele. Sequence comparison is typically performed using the BLAST or BLAST 2.0 algorithm with default parameters, discussed below.

CNG2B polymorphic variants, interspecies homologs, and alleles can be confirmed by expressing or co-expressing the putative CNG2B polypeptide monomer and examining whether it forms a cation channel with CNG family functional and biochemical characteristics. This assay is used to demonstrate that a protein having about 60% or greater, 65%, 70%, 75%, 80%, preferably 85%, 90%, or 95% or greater amino acid identity to CNG2B shares the same functional characteristics as CNG2B and is therefore a species of CNG2B. Typically, human CNG2B having the amino acid sequence of SEQ ID NO:1 is used as a positive control in comparison to the putative CNG2B protein to demonstrate the identification of a CNG2B polymorphic variant, ortholog, conservatively-modified variant, mutant, or allele.

CNG2B nucleotide and amino acid sequence information may also be used to construct models of cyclic nucleotide-gated cation channels in a computer system. These models are subsequently used to identify compounds that can activate or inhibit cyclic nucleotide-gated cation channels comprising CNG2B polypeptides. Such compounds that modulate the activity of channels comprising CNG2B polypeptides can be used to investigate the role of CNG2B polypeptides in the modulation of channel activity and in channel diversity.

The isolation of biologically active CNG2B for the first time provides a means for assaying for inhibitors and activators of cyclic nucleotide-gated cation channels that comprise CNG2B subunits. Biologically active CNG2B polypeptides are useful for testing inhibitors and activators of cyclic nucleotide-gated cation channels comprising subunits of CNG2B, using in vivo and in vitro expression that measure, e.g., changes in voltage or current. Such activators and inhibitors identified using a cation channel comprising at least one CNG2B subunit, optionally up to four CNG2B subunits, can be used to further study cyclic nucleotide-gating, channel kinetics and conductance properties of cation channels. Such activators and inhibitors are useful as pharmaceutical agents for treating diseases involving abnormal ion flux, e.g., disorders, including neurological disorders, as described above. Methods of detecting CNG2B nucleic acids and polypeptides and expression of channels comprising CNG2B polypeptides are also useful for diagnostic applications for diseases involving abnormal ion flux, e.g., as described above. For example, chromosome localization of the gene encoding human CNG2B can be used to identify diseases caused by and associated with CNG2B. Methods of detecting CNG2B are also useful for examining the role of CNG2B in channel diversity and modulation of channel activity.

II. Definitions

As used herein, the following terms have the meanings ascribed to them unless specified otherwise.

"CNG2B" refers to a polypeptide that is a subunit or monomer of a cyclic nucleotide gated cation channel, and a member of the CNG family. When CNG2B is part of a cation channel, e.g., a homomultimeric or heteromultimeric cation channel, the channel has the characteristic of cyclic nucleotide gating or nitric oxide gating. The term CNG2B therefore refers to CNG2B polymorphic variants, alleles, mutants, and interspecies homologs that: (1) have an amino acid subsequence that has greater than about 60% amino acid sequence identity, 65%, 70%, 75%, 80%, 85%, 90%, preferably 95%, 96%, 97%, 98% or 99% or greater amino acid sequence identity, to a CNG2B sequence of SEQ ID NO:1; (2) bind to antibodies, e.g., polyclonal antibodies, raised against an immunogen comprising an amino acid sequence of SEQ ID NO:1 or a fragment or conservatively modified variants thereof; (3) specifically hybridize under stringent hybridization conditions to a sequence of SEQ ID NOS:2–3 and fragments and conservatively modified variants thereof; (4) have a nucleic acid subsequence that has greater than about 90%, preferably greater than about 96%, 97%, 98%, 99%, or higher nucleotide sequence identity to SEQ ID NO:2 or SEQ ID NO:3; or (5) are amplified by primers that specifically hybridize under stringent hybridization conditions to the same sequence as a primer set selected from the group consisting of SEQ ID NOS:4–13.

The phrase "cyclic nucleotide-gated" activity or "cyclic nucleotide-gating" refers to a characteristic of a cation channel composed of individual polypeptide monomers or subunits. Generally, cyclic-nucleotide-gated cation channels are a class of non-selective cation channels that are opened by direct binding of cyclic nucleotides such as cGMP and cAMP. CNG channels are highly permeable to $Na^+$ and $Ca^{2+}$, and their activation leads to depolarization and increases in internal $Ca^{2+}$ concentrations. CNG channels can thus link changes in cytoplasmic cyclic nucleotide levels to changes in cellular excitability, secretion of neurotransmitters, and/or stimulation of calcium-dependent pathways. CNG channels play an important role in sensory signal transduction in numerous cells, e.g., cells throughout the central nervous system, in response to primary sensory stimuli such as light and aerosolized or dissolved molecules.

In photoreceptor cells, CNG channels are open in darkness due to a high basal concentration of cGMP, causing a tonic depolarization of the membrane and constitutive neurotransmitter release. Upon stimulation by light, cGMP levels drop, closing the CNG channels, and in turn causing a hyperpolarization of the membrane, a drop in the internal $Ca^{2+}$ concentration, and a decrease in neurotransmitter release. CNG channels may also interact with second messenger systems such as the nitric oxide pathway. In some cases, NO may substitute for cyclic nucleotides in gating these channels (see, e.g., Broillet, et al., *Neuron* 18:951–958 (1997)).

"Homomeric channel" or "homomultimeric channel" refers to a CNG channel composed of identical alpha subunits, whereas "heteromeric channel" or "heteromultimeric channel" refers to a CNG channel composed of at least one CNG alpha subunit, e.g., CNG2B, plus at least one other type of alpha or beta subunit.

An "alpha subunit" is a polypeptide monomer that is an essential subunit of a CNG cation channel, as at least one alpha subunit is required to create a functional channel. Alpha subunits can form a homomultimeric cationic channel, or can form a heteromultimeric channel comprising other beta subunits or other heterologous alpha subunits. Any particular alpha subunit may participate in a variety of channel types in an organism or in a cell, e.g., forming homomultimeric channels in one cell type, forming a heteromultimeric channel with a beta subunit in a second cell type, and forming a third heteromultimeric channel with a heterologous alpha subunit in a third cell type.

A "beta subunit" is a polypeptide monomer that is an auxiliary subunit of a CNG cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "functional effects" in the context of assays for testing compounds affecting a channel comprising a CNG2B polypeptide includes the determination of any parameter that is indirectly or directly under the influence of the channel. It includes e.g., direct, physical effects, such as ligand binding, and indirect, chemical or phenotypic effects, e.g., changes in ion flux and membrane potential, and other physiologic effects such as increases or decreases of transcription or hormone release. "Functional effects" include in vitro (biochemical or ligand binding assays using, e.g., isolated protein, cell lysates or cell membranes), in vivo (cell- and animal-based assays), and ex vivo activities.

"Determining the functional effect" refers to examining the effect of a compound that has a direct physical effect on a CNG2B subunit or channel comprising a CNG2B subunit, e.g., ligand binding, or indirect chemical or phenotypic effects on channel comprising a CNG2B subunit, e.g., increases or decreases ion flux in a cell or cell membrane. The ion flux can be any ion that passes through a channel and analogues thereof, e.g., potassium, rubidium. Preferably, the term refers to the functional effect of the compound on the channels comprising CNG2B, e.g., changes in ion flux including radioisotopes, current amplitude, membrane potential, current flow, conductance, transcription, protein binding, phosphorylation, dephosphorylation, second messenger concentrations (cAMP, cGMP, $Ca^{2+}$, $IP_3$), ligand binding, changes in ion concentration, and other physiological effects such as hormone and neurotransmitter release, as well as changes in voltage and current. Such functional effects can be measured by any means known to those skilled in the art, e.g., patch clamping, voltage-sensitive dyes, ion sensitive dyes, whole cell currents, radioisotope efflux, inducible markers, and the like.

"Inhibitors," "activators" or "modulators" of cyclic nucleotide-gated cation channels comprising a CNG2B polypeptide refer to inhibitory or activating molecules identified using in vitro and in vivo assays for CNG2B channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing a CNG2B polypeptide in cells or cell membranes and then measuring flux of ions through the channel and determining changes in polarization or $Ca^{2+}$ concentration (i.e., electrical potential). Alternatively, cells expressing endogenous CNG2B channels can be used in such assays. To examine the extent of inhibition, samples or assays comprising a CNG2B channel are treated with a potential activator or inhibitor and are compared to control samples without the inhibitor. Control samples (untreated with inhibitors) are assigned a relative CNG2B activity value of 100%. Inhibition of channels comprising CNG2B is achieved when the CNG2B activity value relative to the control is about 90%, preferably 50%, more preferably 25–0%. Activation of channels comprising CNG2B is achieved when the CNG2B activity value relative to the control is 110%, more preferably 150%, most preferably at least 200–500% higher or 1000% or higher.

"Biologically active" CNG2B polypeptides refers to CNG2B polypeptides that have the ability to form a cation channel having the characteristic of cyclic nucleotide-gating tested as described herein.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated CNG2B nucleic acid is separated from open reading frames that flank the CNG2B gene and encode proteins other than CNG2B. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to directly or indirectly modulation lymphocyte activation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 5000 daltons, preferably less than about 2000 daltons, preferably between about 100 to about 1000 daltons, more preferably between about 200 to about 500 daltons.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, 65%, 70%, 75%, 80%, preferably 85%, 90%, 91%, 92%, 93%, 94%, 95%, 96%, 97%, 98%, 99% or higher identity to an amino acid sequence such as SEQ ID NO:1 or a nucleotide sequence such as SEQ ID NO:2 or SEQ ID NO:3), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison-algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to CNG2B nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci.* USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min. Protocols and guidelines for low and high stringency amplification reactions are provided, e.g., in Innis et al (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al, *Biotechnology* 10:779–783 (1992)).

An "anti-CNG2B" antibody is an antibody or antibody fragment that specifically binds a polypeptide encoded by a CNG2B gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to CNG2B, as shown in SEQ ID NO:1, or splice variants, or portions thereof, can be selected to obtain only those polyclonal antibodies that are specifically immunoreactive with CNG2B and not with other proteins. This selection may be achieved by subtracting out antibodies that cross-react with molecules such as other CNG family members. In addition, polyclonal antibodies raised to CNG2B polymorphic variants, alleles, orthologs, and conservatively modified variants can be selected to obtain only those antibodies that recognize CNG2B, but not other CNG family members. In addition, antibodies to human CNG2B but not other CNG2B orthologs can be selected in the same manner. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains CNG2B polypeptides or nucleic acid encoding a CNG2B protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolating a Gene Encoding a CNG2B Polypeptide

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding CNG2B Polypeptides In general, the nucleic acid sequences encoding CNG2B and related nucleic acid sequence homologs are cloned from cDNA and genomic DNA libraries or isolated using amplification techniques with oligonucleotide primers. For example, CNG2B sequences are typically isolated from human nucleic acid (genomic or cDNA) libraries by hybridizing with a nucleic acid probe or polynucleotide, the sequence of which can be derived from SEQ ID NOS:2–3. A suitable tissue from which CNG2B RNA and cDNA can be isolated is the central nervous system (CNS). Preferably, the template for the amplification is first strand cDNA made from some part of the human CNS.

Amplification techniques using primers can also be used to amplify and isolate CNG2B from DNA or RNA. The following primers can also be used to amplify a sequence of human CNG2B:

| | |
|---|---|
| GCAGATCTTTCAGAACTGTGAGGCCA | (SEQ ID NO:4) |
| CCTGCCCTCTTCATCTTTGGAAGTTC | (SEQ ID NO:5) |
| GCCAACATCAAGAGCCTAGGTTATTC | (SEQ ID NO:6) |
| GGATGATCTACAGACCAAGTTTGCTCG | (SEQ ID NO:7) |
| ATGAGCCAGGACACCAAAGTGAAGAC | (SEQ ID NO:8) |
| GTTGATGATGCTGATCTCCCCAAAG | (SEQ ID NO:9) |
| GGATGATGAGGTTATACATGACTGGG | (SEQ ID NO:10) |
| AGGCTAGCAACTTCCTGGCCTTGGAT | (SEQ ID NO:11) |
| GCGAAAGCTTCCACCATGAGCCAGGACACCA AAGTG | (SEQ ID NO:12) and |
| CATGTCTAGAATGGGGATGGGGTCA CTCTGGACCT | (SEQ ID NO:13). |

These primers can be used, e.g., to amplify either the full length sequence or a probe of one to several hundred nucleotides, which is then used to screen a library for full-length CNG2B. For example, Oligo 1 (SEQ ID NO:4) can be used with Oligo 2 (SEQ ID NO:5) to produce a 657 bp band, and Oligo 9 (SEQ ID NO:12) and Oligo 10 (SEQ ID NO:13) can be used to amplify the entire coding region. Further, in conjunction with other oligos, Oligo 9 can be used with Oligos 2, 6, 7 or 8 (SEQ ID NOs:5, 9, 10 or 11) to produce bands of approximately 1.7 Kb, 1.28 Kb, 170 bp, or 90 bp, respectively. Similarly, Oligo 10 can be used with Oligos 1, 3, or 4 (SEQ ID NOs:4, 6 or 7) to produce fragments of approximately 715 bp, 455 bp, or 240 bp, respectively. Only the nucleotides in bold type in oligos 9 and 10 are required for CNG2B amplification, and each of the above product sizes are approximate.

Nucleic acids encoding CNG2B and other CNG2B family members can also be isolated from expression libraries using antibodies as probes. Such polyclonal or monoclonal antibodies can be raised using the sequence of SEQ ID NO:1, or any immunogenic portion thereof.

CNG2B polymorphic variants, orthologs, and alleles that are substantially identical to the conserved region of CNG2B can be isolated using CNG2B nucleic acid probes and oligonucleotides under stringent hybridization conditions, by screening libraries. Alternatively, expression libraries can be used to clone CNG2B and CNG2B polymorphic variants, orthologs, and alleles by detecting expressed homologs immunologically with antisera or purified antibodies made against human CNG2B or portions thereof, which also recognize and selectively bind to the CNG2B homolog.

To make a cDNA library, one should choose a source that is rich in CNG2B mRNA, e.g., the central nervous system. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, Gene 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180–182 (1977). Colony hybridization is carried out as generally described in Grunstein et al., Proc. Natl. Acad. Sci. USA., 72:3961–3965 (1975).

An alternative method of isolating CNG2B nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of human CNG2B directly from mRNA, from cDNA, from genomic libraries or cDNA libraries. Degenerate oligonucleotides can be designed to amplify CNG2B homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of CNG2B encoding mRNA in physiological samples, for nucleic acid sequencing, or for other purposes. Genes amplified by the PCR reaction can be purified from agarose gels and cloned into an appropriate vector.

Gene expression of CNG2B can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology and the like.

Synthetic oligonucleotides can be used to construct recombinant CNG2B genes for use as probes or for expression of protein. This method is performed using a series of overlapping oligonucleotides usually 40–120 bp in length, representing both the sense and non-sense (antisense) strands of the gene. These DNA fragments are then annealed, ligated and cloned. Alternatively, amplification techniques can be used with precise primers to amplify a specific subsequence of the CNG2B gene. The specific subsequence is then ligated into an expression vector.

The gene for CNG2B is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding CNG2B, one typically subclones the gene into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al., supra. Bacterial expression systems for expressing the CNG2B protein are available in, e.g., E. coli, Bacillus sp., and Salmonella (Palva et al., Gene 22:229–235 (1983); Mosbach et al., Nature 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the CNG2B encoding nucleic acid in host cells. A typical expression cassette thus contains a promoter operably linked to the nucleic acid sequence encoding CNG2B and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a CNG2B encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical—any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of CNG2B protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing CNG2B.

After the expression vector is introduced into the cells, the transfected cells are cultured under conditions favoring expression of CNG2B, which is recovered from the culture using standard techniques identified below.

IV. Purification of CNG2B Polypeptides

Either naturally occurring or recombinant CNG2B can be purified for use in functional assays. Naturally occurring CNG2B monomers can be purified, e.g., from human tissue such as the central nervous system or any other source of a CNG2B homolog. Recombinant CNG2B monomers can be purified from any suitable expression system.

The CNG2B monomers may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant CNG2B monomers are being purified. For example, proteins having established molecular adhesion properties can be reversibly fused to the CNG2B monomers. With the appropriate ligand, the CNG2B monomers can be selectively adsorbed to a purification column and then freed from the column in a relatively pure form. The fused protein is then removed by enzymatic activity. Finally the CNG2B monomers could be purified using immunoaffinity columns.

A. Purification of CNG2B Monomers from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the CNG2B monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al, supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human CNG monomers are separated from other bacterial proteins by standard separation techniques, e.g., with Ni-NTA agarose resin.

Alternatively, it is possible to purify the CNG2B monomers from bacteria periplasm. After lysis of the bacteria, when the CNG2B monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying CNG2B Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the CNG2B monomers (e.g., approximately 92 kD) can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The CNG2B monomers can also be separated from other proteins on the basis of size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of CNG2B Polypeptides

In addition to the detection of CNG2B genes and gene expression using nucleic acid hybridization technology, one can also use immunoassays to detect the CNG2B monomers of the invention. Immunoassays can be used to qualitatively or quantitatively analyze the CNG2B monomers. A general overview of the applicable technology can be found in Harlow & Lane, *Antibodies: A Laboratory Manual* (1988).

A. Antibodies to CNG2B Monomers

Methods of producing polyclonal and monoclonal antibodies that react specifically with CNG2B monomers, or CNG2B monomers from particular species such as human CNG2B, are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of CNG2B monomers may be used to produce antibodies specifically reactive with CNG2B monomers. For example, recombinant CNG2B monomers or an antigenic fragment thereof can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-CNG family proteins and other CNG family proteins, using a competitive binding immunoassay. Specific polyclonal antisera and monoclonal antibodies will usually bind with a $K_d$ of at least about 0.1 mM, more usually at least about 1 M, preferably at least about 0.1 M or better, and most preferably, 0.01 M or better. Antibodies specific only for a particular CNG2B ortholog, such as human CNG2B, can also be made, by subtracting out other cross-reacting orthologs from a species such as a non-human mammal.

Once the specific antibodies against a CNG2B are available, the CNG2B can be detected by a variety of immunoassay methods. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The CNG2B polypeptides of the invention can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., $7^{th}$ ed. 1991). Immunological binding assays (or immunoassays) typically use an antibody that specifically binds to a protein or antigen of choice (in this case the CNG2B or an antigenic subsequence thereof). The antibody (e.g., anti-CNG2B) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled CNG2B polypeptide or a labeled anti-CNG2B antibody. Alternatively, the labeling agent may be a third moiety, such a secondary antibody, which specifically binds to the antibody/CNG2B complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting the CNG2B in samples may be either competitive or noncompetitive. Noncompetitive immunoassays are assays in which the amount of antigen is directly measured. In one preferred "sandwich" assay, for example, the anti-CNG2B subunit antibodies can be bound directly to a solid substrate on which they are immobilized. These immobilized antibodies then capture CNG2B present in the test sample. The CNG2B monomers are thus immobilized and then bound by a labeling agent, such as a second CNG2B antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the CNG2B present in the sample is measured indirectly by measuring the amount of known, added (exogenous) CNG2B displaced (competed away) from an anti-CNG2B antibody by the unknown CNG2B present in a sample. In one competitive assay, a known amount of the CNG2B is added to a sample and the sample is then contacted with an antibody that specifically binds to the CNG2B. The amount of exogenous CNG2B bound to the antibody is inversely proportional to the concentration of the CNG2B present in the sample. In a particularly preferred embodiment, the antibody is immobilized on a solid substrate. The amount of CNG2B bound to the antibody may be determined either by measuring the amount of CNG2B present in a CNG2B/antibody complex, or alternatively by measuring the amount of remaining uncomplexed protein. The amount of CNG2B may be detected by providing a labeled CNG2B molecule.

A hapten inhibition assay is another preferred competitive assay. In this assay the known CNG2B is immobilized on a solid substrate. A known amount of anti-CNG2B antibody is added to the sample, and the sample is then contacted with the immobilized CNG2B. The amount of anti-CNG2B antibody bound to the known immobilized CNG2B is inversely proportional to the amount of CNG2B present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations for CNG2B. For example, a CNG2B protein at least partially corresponding to an amino acid sequence of SEQ ID NO:1 or an immunogenic region thereof can be immobilized to a solid support. Other proteins such as other CNG family members are added to the assay so as to compete for binding of the antisera to the immobilized antigen. The ability of the added proteins to compete for binding of the antisera to the immobilized protein is compared to the ability of the CNG2B or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. Antibodies that specifically bind only to particular orthologs of CNG2B, such as human CNG2B, can also be made using this methodology.

The immunoabsorbed and pooled antisera are then used in a competitive binding immunoassay as described above to compare a second protein, thought to be perhaps an allele, ortholog, or polymorphic variant of CNG2B, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by CNG2B that is required to inhibit 50% of binding, then the second protein is said to specifically bind to the polyclonal antibodies generated to the respective CNG2B immunogen.

Other Assay Formats

Western blot (immunoblot) analysis is used to detect and quantify the presence of the CNG2B in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind CNG2B. The anti-CNG2B antibodies specifically bind to CNG2B on the solid support. These antibodies may be directly labeled or alternatively may be subsequently detected using labeled antibodies (e.g., labeled sheep anti-mouse antibodies) that specifically bind to the anti-CNG2B antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$p), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize CNG2B, or secondary antibodies that recognize anti-CNG2B antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of CNG2B

A. Assays

Introduction

Human CNG2B and CNG2B alleles, orthologs, and polymorphic variants are subunits of cation channels. The activity of a cation channel comprising CNG2B can be assessed using a variety of in vitro and in vivo assays, e.g., measuring current, measuring membrane potential, measuring ion flux, e.g., cations such as sodium or calcium, measuring ion concentration, measuring second messengers and transcription levels, measuring ligand binding, and using, e.g., voltage-sensitive dyes, ion sensitive dyes such as cation (e.g., sodium or calcium) sensitive dyes, radioactive tracers, and patch-clamp electrophysiology.

In preferred embodiments, the activity of a CNG cation channel will be detected by detecting cation, e.g., calcium or sodium, concentration or flux using an ion (e.g., calcium or sodium) specific dye, e.g., a fluorescent dye. Any such dye, a large number of which are well known to those of skill in the art, can be used. For example, any of a number of fluorescent probes that show a spectral response upon binding $Ca^{2+}$ allowing the detection of changes in intracellular free $Ca^{2+}$ concentrations using fluorescence microscopy, flow cytometry or fluorescence spectroscopy, can be used.

Furthermore, such assays can be used to test for inhibitors and activators of channels comprising CNG2B. Such modulators of a cation channel are useful for treating various disorders involving cation channels, e.g., neurological disorders, e.g., of the central nervous system. Such modulators are also useful for investigation of the channel diversity provided by CNG family members and the regulation/modulation of cation channel activity provided by CNG family members such as CNG2B.

Modulators of the CNG cation channels are tested using biologically active CNG2B, either recombinant or naturally occurring, preferably human CNG2B. CNG2B can be isolated, co-expressed or expressed in a cell, or expressed in a membrane derived from a cell. In such assays, CNG2B can be expressed alone to form a homomultimeric cation channel, or in combination with other CNG proteins, including alpha and/or beta subunits, to form a heteromultimeric cation channel. Preferably, the CNG2B polypeptide that is a part of the cation channel used in the assay will have the sequence displayed in SEQ ID NO:1 or a conservatively modified variant thereof. Generally, the amino acid sequence identity of the polypeptide to SEQ ID NO:1 will be at least 60%, 65%, 70%, 75%, 80%, preferably 85%, or 90%, most preferably at least 95% or higher.

Modulation is tested using one of the in vitro or in vivo assays described herein Samples or assays that are treated with a potential cation channel inhibitor or activator are compared to control samples without the test compound, to examine the extent of modulation. Often, such assays are performed in the presence of a cyclic nucleotide, e.g., cAMP or cGMP, and the ability of the test agent to modulate the effect of the cyclic nucleotide on the channel is detected.

Control samples (untreated with activators or inhibitors) are assigned a relative cation channel activity value of 100. Inhibition of channels comprising a CNG2B polypeptide is achieved when the cation channel activity value relative to the control is about 90%, preferably 50%, more preferably 25%. Activation of channels comprising a CNG2B polypeptide is achieved when the cation channel activity value relative to the control is 110%, more preferably 150%, more preferable 200% higher. Compounds that increase the flux of ions will cause a detectable increase in the ion current density by increasing the probability of a channel comprising a CNG2B polypeptide being open, by decreasing the probability of it being closed, by increasing conductance through the channel, and/or by allowing the passage of ions.

In Vitro Assays

Assays to identify compounds with cation channel modulating activity can be performed in vitro, e.g., binding assays and biochemical assays. Purified recombinant or naturally occurring CNG2B protein, or a channel comprising CNG2B protein, can be used in the in vitro methods of the invention. In addition to purified CNG2B protein or channel comprising the same, the recombinant or naturally occurring CNG2B protein can be part of a cellular lysate or a cell membrane. As described below, the assay can be either solid state or soluble. Preferably, the protein or membrane is bound to a solid support, either covalently or non-covalently. Often, the in vitro assays of the invention are ligand or toxin binding or ligand affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein or channel. Cell membranes or lysates can also be used to measure changes in polarization (i.e., electrical potential) of the cell or membrane expressing the cation channel comprising a CNG2B polypeptide, as described below.

In Vivo Cell- or Membrane Based Assays

Changes in ion flux may be assessed by determining changes in polarization (i.e., electrical potential) of the cell or membrane expressing the cation channel comprising a CNG2B polypeptide. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using standard methodology (see, e.g., Hamil et al., *PFlugers. Archiv.* 391:85 (1981). Other known assays include fluorescence assays using ion sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)).

Examples of such dyes useful for the detection of calcium include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site (www.probes.com) for Molecular Probes, Eugene, see, also, Nuccitelli, ed., *Methods in Cell Biology, Volume 40: A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999)). Examples of sodium indicators include, but are not limited to, SBFI, and Sodium Green (see, e.g., Molecular probes catalog or Internet site; Mason, supra).

Assays for compounds capable of inhibiting or increasing cation flux through the channel proteins comprising a CNG2B polypeptide can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or calcium ions. The ions can be measured in a variety of standard ways. They can be measured directly by concentration changes of the ions, e.g., changes in intracellular concentrations, e.g., using any of the dyes listed supra, or radiolabeled ions, or indirectly by membrane potential. Consequences of the test compound on ion flux can be quite varied. Accordingly, any suitable physiological change can be used to assess the influence of a test compound on the channels of this invention. The effects of a test compound can be measured by a toxin binding assay. One can also measure a variety of effects such as transmitter release (e.g., dopamine), intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as cyclic nucleotides.

CNG2B orthologs, alleles, polymorphic variants, and conservatively modified variants will generally confer substantially similar properties on a channel comprising a CNG2B polypeptide, as described above. In a preferred embodiment, the cell placed in contact with a compound that is suspected to be a CNG2B homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to CNG2B are considered homologs or orthologs of CNG2B.

Animal Models

Animal models also find use in screening for cation channel modulators. Transgenic animal technology, including gene knockout technology as a result of homologous recombination with an appropriate gene targeting vector, or gene overexpression, will result in the absence or increased expression of the CNG2B protein. When desired, tissue-specific expression or knockout of the CNG2B protein may be necessary. Transgenic animals generated by such methods find use as animal models of abnormal ion flux and are additionally useful in screening for modulators of cation channels.

B. Modulators

The compounds tested as modulators of CNG channels comprising a CNG2B subunit can be any small organic molecule, or a biological entity, such as a protein, peptide, sugar, nucleic acid, oligonucleotide, or lipid. Alternatively, modulators can be genetically altered versions of a CNG2B subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a CNG channel comprising a human CNG2B subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100–about 1500 different compounds. It is possible to assay many plates per day; assay screens for up to about 6,000, 20,000, 50,000, or 100,000 or more different compounds are possible using the integrated systems of the invention.

C. Solid State and Soluble High Throughput Assays

In one embodiment the invention provides soluble assays using cation channels comprising a CNG2B polypeptide, a membrane comprising a CNG2B cation channel, or a cell or tissue expressing cation channels comprising a CNG2B polypeptide, either naturally occurring or recombinant. In another embodiment, the invention provides solid phase based in vitro assays in a high throughput format, where a CNG2B cation channel is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–about 1500 different compounds. It is possible to assay many plates per day; assay screens for up to about 6,000, 20,000, 50,000, or more than 100,000 different compounds are possible using the integrated systems of the invention.

The channel of interest, or a cell or membrane comprising the channel of interest, can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I*(1993)). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

VII. Computer Assisted Drug Design Using CNG2B

Yet another assay for compounds that modulate the activities of a CNG2B channel involves computer assisted drug design, in which a computer system is used to generate a three-dimensional structure of CNG2B based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other cation channel subunits. These regions are then used to identify ligands that bind to the protein or region where CNG2B interacts with other cation channel subunits.

The three-dimensional structural model of the protein is generated by entering channel protein amino acid sequences of at least 25, 50, 75, 100, 150, or 200 amino acid residues or corresponding nucleic acid sequences encoding a CNG2B monomer into the computer system. The amino acid sequence of each of the monomers is selected from the group consisting of SEQ ID NO:1, conservatively modified versions thereof, and immunogenic portions thereof. The amino acid sequence represents the primary sequence or subsequence of each of the proteins, which encodes the structural information of the protein. At least 25, 50, 75, 100, 150, or 200 residues of the amino acid sequence (or a nucleotide sequence encoding at least about 25, 50, 75, 100, 150, or 200 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric cation channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the CNG2B protein to identify ligands that bind to CNG2B. Binding affinity between the protein and ligands is determined using energy terms to determine which ligands have an enhanced probability of binding to the protein.

Computer systems are also used to screen for mutations, polymorphic variants, alleles and interspecies homologs of CNG2B genes. Such mutations can be associated with disease states. Once the variants are identified, diagnostic assays can be used to identify patients having such mutated genes associated with disease states. Identification of the mutated CNG2B genes involves receiving input of a first nucleic acid, e.g., SEQ ID NOS:2–3, or an amino acid sequence encoding CNG2B, e.g., SEQ ID NO:1, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in CNG2B genes, preferably human CNG2B genes, and mutations associated with disease states. The first and second sequences described above can be saved on a computer readable substrate.

Nucleic acids encoding CNG2B monomers can be used with high density oligonucleotide array technology (e.g., GeneChip™) to identify CNG2B homologs, orthologs, alleles, conservatively modified variants, and polymorphic variants in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

VIII. Cellular Transfection and Gene Therapy

The present invention provides the nucleic acids of CNG2B genes for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for CNG2B, under the control of a promoter, then expresses a CNG2B monomer of the present invention, thereby mitigating the effects of absent, partial inactivation, or abnormal expression of the CNG2B gene. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357:455–460 (1992); Van Brunt, *Biotechnology* 6(10): 1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GalV), simian immunodeficiency virus (SIV), human immunodeficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hemonat & Muzyczka, *Proc. Natl. Acad. Sci. U.S.A.* 81:6466–6470 (1984); and Samulski et al., *J. Virol.* 63:03822–3828 (1989).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* 17$^{th}$ ed., 1989). Administration can be in any convenient manner, e.g., by injection, oral administration, inhalation, or transdermal application.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the CNG channels comprising a CNG2B subunit, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

X. Kits

Human CNG2B and its homologs are useful tools for examining expression and regulation of cation channels. Human CNG2B-specific reagents that specifically hybridize to CNG2B nucleic acid, such as CNG2B probes and primers, and CNG2B-specific reagents that specifically bind to the CNG2B protein, e.g., CNG2B antibodies, are used to examine expression and regulation.

Nucleic acid assays for the presence of CNG2B DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, CNG2B protein can be detected with the various immunoassay techniques described above. The test sample is typically compared to both a positive control (e.g., a sample expressing recombinant CNG2B monomers) and a negative control.

The present invention also provides for kits for screening modulators of the cation channels of the invention. Such kits can be prepared from readily available materials and reagents. For example, such kits can comprise any one or more of the following materials: CNG2B monomers, reaction tubes, and instructions for testing the activities of cation channels containing CNG2B. A wide variety of kits and components can be prepared according to the present invention, depending upon the intended user of the kit and the particular needs of the user. For example, the kit can be tailored for in vitro or in vivo assays for measuring the activity of a cation channel comprising a CNG2B monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

A. Identification of Human CNG2B

Multiple exons of human CNG2B were identified from public genomic data (accession numbers AC022762 and AC021935) using TBLASTN searches with cyclic nucleotide-gated channel protein sequences. The 5' and 3' exons of the CNG2B coding sequence could not be identified in these searches. Oligonucleotides based on the AC022762 and AC021935 sequences were designed to clone a full-length CNG2B cDNA.

An approximately 657 bp band from the CNG2B gene was amplified from first strand cDNA prepared from the human brain, demonstrating expression in the central nervous system. The oligos used to amplify this band were 5'-(1)GCAGATCTTCCAGAACTGTAAGGCCA (SEQ ID NO:14) (sense) and 5'-(2)CCTGCCCTCTTCATCTTTGGAAGTTC (SEQ ID NO:5) (antisense).

The complete 3' end of CNG2B was amplified by standard 3' RACE PCR techniques from human brain cDNA in two successive rounds. In the first round the gene specific primer used was 5'-(3) GCCAACATCAAGAGCCTAGGTTATTC (SEQ ID NO:6) (sense). This reaction was then reamplified with a nested gene specific oligo 5'-(4) GGATGATCTACA-GACCAAGTTTGCTCG (SEQ ID NO:7) (sense) to produce a fragment of approximately 765bp in length that, when sequenced, was found to include the complete 3' end of the human CNG2B mRNA. The sequence of this fragment overlapped with the original 657 bp CNG2B fragment to provide contiguous sequence. Most of the 5' end of the CNG2B coding sequence was amplified from human brain cDNA using a degenerate sense strand oligo based on the N-terminal amino acid sequence of rat OCNC2 protein (5'-(5) ATGAGCCAGGACGGNAARGTNAARAC (SEQ ID NO:15)) and an antisense primer specific to human CNG2B (5'-(6) GTTGATGATGCTGATCTCCCCAAAG (SEQ ID NO:9)). This reaction produced a fragment of approximately 1.2 Kb with a sequence highly homologous to rat OCNC2. Two rounds of standard 5' RACE PCR were then used to complete the 5' coding sequence of human CNG2B and to identify the initiator methionine codon. The CNG2B-specific oligo 5'-(7) GGATGATGAGGTTATA-CATGACTGGG (SEQ ID NO:10) (antisense) was used in the first round of RACE PCR. This reaction was reamplified using the nested CNG2B specific oligo 5'-(8) AGGCTAG-CAACTTCCTGGCCTTGGAT (SEQ ID NO:11) (antisense). An approximately 410 bp fragment containing the complete 5' end of CNG2B including the start codon was isolated. This fragment overlapped the 1.2 Kb PCR fragment described above. The entire contiguous coding region of the CNG2B mRNA was determined by assembling these two fragments with the original 657 bp internal fragment and the 765 bp 3' RACE product.

The entire coding region of human CNG2B was then isolated in a single fragment using oligonucleotides overlapping the CNG2B coding sequence ends. The oligonucleotides used were (SEQ ID NO:12)
5'-(9)GCGAAAGCTTCCACCATGAGCCAGGACACCAAAGTG
(sense) and (SEQ ID NO:13)
5'-(10)CATGTCTAGAATGGGGATGGGG<u>TCA</u>CTCTGGACCT
(antisense).

The first oligonucleotide includes the initiator methionine and the first 21 coding nucleotides of the CNG2B gene. Upstream are a HindIII restriction enzyme site for subcloning into plasmid vectors and a Kozak consensus sequence to boost translation. All nucleotides corresponding to CNG2B are in bold type. The second oligonucleotide is from the 3' sequence of CNG2B and includes an XbaI restriction enzyme site for subcloning. All nucleotides in bold correspond to the 3' end sequence of CNG2B. The stop codon is underlined. It is important to note that only the nucleotides that are in bold type from the two oligos above are necessary for amplification of CNG2B. The preferred template for the amplification is first strand cDNA from the human brain. The amplification conditions used were as follows: 24 cycles of 95° C. for 15 seconds, 72–60° C. for 15 seconds (temperature was dropped 0.5° C. each successive cycle), 72° C. for 3 minutes, followed by 20 cycles of 95° C. for 15 seconds, 60° C. for 15 seconds, and 72° C. for 3 minutes. An approximately 1.73 Kb band corresponding to the entire coding region of CNG2B was obtained and confirmed by sequencing.

The predicted molecular weight of the human CNG2B protein is about 66 Kd, with a range of approximately 60 Kd–80 Kd, preferably about 61–71 Kd.

B. Comparison of Human CNG2B With Other CNG Genes

An alignment of the deduced amino acid sequence of CNG2B to rat OCNC2 (Bradley, et al., *Proc. Natl. Acad. Sci. U.S.A.* 91, 8890–8894, 1994) is shown in FIG. 1. The amino acid sequences of human CNG2B and rat OCNC2 are 93% identical, indicating that they are likely to be orthologous genes. Additional evidence supporting this idea is that human CNG2B is much more homologous to rat OCNC2 than any of the other cloned CNG channels. Most of the differences between the two amino acid sequences are clustered at the amino and carboxy termini. Human CNG2B and rat OCNC2 are less than 90% identical on the nucleic acid level.

The human CNG2B gene appears to be orthologous to the rat OCNC2 gene, suggesting that it serves a similar functional role. In support of this idea is our evidence for expression of human CNG2B in the brain, where there is widespread expression of rat OCNC2 (Kingston, et al., *Synapse* 32:1–12 (1999). The rat OCNC2 gene was originally classified as a CNG beta subunit because it is functionally insensitive to cyclic nucleotides when expressed as a homomultimer (Bradley, et al., *Proc. Nat. Acad. Sci.* 91:8890–8894 (1994). Instead, it was shown to form functional heteromultimeric channels with the rat OCNC 1 alpha subunit which participates in olfactory transduction (Bradley, et al., *Proc. Nat. Acad. Sci.* 91:8890–8894 (1994). This alpha and beta heteromultimeric channel showed increased sensitivity to cAMP closely resembling the native CNG olfactory channel (Linman, et al., *Neuron* 13:611–621 (1994). However, other studies have shown that functional homomeric rat OCNC2 channels may exist in the brain, and that they are nitric oxide-sensitive (Broillet, et al., *Neuron* 18:951–958 (1997)). This finding, combined with the widespread distribution of rat OCNC2 in the brain and its high permeability to $Ca^{2+}$, suggest that these channels may play a role in neuronal signaling and synaptic plasticity (Bradley, et al., *JNC* 17:1993–2005 (1997). The ability of rat OCNC2 to form functional homomultimeric channels is consistent with the fact that it shares greater homology with CNG alpha subunits than with CNG beta subunits. Rat OCNC2 and human CNG2B are thus likely to be functionally significant both as heteromultimers and as homomultimers.

What is claimed is:

1. An isolated nucleic acid encoding a polypeptide comprising a subunit of a cation channel, the polypeptide:
   (i) forming, with at least one cyclic nucleotide gated cation channel (CNG) alpha subunit, a cation channel having the characteristic of cyclic nucleotide-gating; and
   (ii) comprising an amino acid sequence of SEQ ID NO:1.

2. The nucleic acid of claim 1, wherein the nucleic acid comprises a nucleotide sequence of SEQ ID NO:2 or SEQ ID NO:3.

3. An isolated nucleic acid encoding a cyclic nucleotide gated cation channel (CNG) 2B polypeptide, the nucleic acid comprising a nucleotide sequence of SEQ ID NO:2 or SEQ ID NO:3, or encoding a polypeptide comprising an amino acid sequence of SEQ ID NO:1.

4. An expression vector comprising the nucleic acid of claim 1.

5. An isolated host cell transfected with the vector of claim 4.

* * * * *

SEQUENCE LISTING

```
<160> NUMBER OF SEQ ID NOS: 16

<210> SEQ ID NO 1
<211> LENGTH: 575
<212> TYPE: PRT
<213> ORGANISM: Homo sapiens
<220> FEATURE:
<223> OTHER INFORMATION: cyclic nucleotide-gated cation channel 2B
      (CNG2B)

<400> SEQUENCE: 1

Met Ser Gln Asp Thr Lys Val Lys Thr Thr Glu Ser Ser Pro Pro Ala
 1               5                  10                  15

Pro Ser Lys Ala Arg Lys Leu Leu Pro Val Leu Asp Pro Ser Gly Asp
            20                  25                  30

Tyr Tyr Tyr Trp Trp Leu Asn Thr Met Val Phe Pro Val Met Tyr Asn
        35                  40                  45

Leu Ile Ile Leu Val Cys Arg Ala Cys Phe Pro Asp Leu Gln His Gly
    50                  55                  60

Tyr Leu Val Ala Trp Leu Val Leu Asp Tyr Thr Ser Asp Leu Leu Tyr
65                  70                  75                  80

Leu Leu Asp Met Val Val Arg Phe His Thr Gly Phe Leu Glu Gln Gly
                85                  90                  95

Ile Leu Val Val Asp Lys Gly Arg Ile Ser Ser Arg Tyr Val Arg Thr
            100                 105                 110

Trp Ser Phe Phe Leu Asp Leu Ala Ser Leu Met Pro Thr Asp Val Val
        115                 120                 125

Tyr Val Arg Leu Gly Pro His Thr Pro Thr Leu Arg Leu Asn Arg Phe
    130                 135                 140

Leu Arg Ala Pro Arg Leu Phe Glu Ala Phe Asp Arg Thr Glu Thr Arg
```

-continued

```
             145                 150                 155                 160
        Thr Ala Tyr Pro Asn Ala Phe Arg Ile Ala Lys Leu Met Leu Tyr Ile
                        165                 170                 175
        Phe Val Val Ile His Trp Asn Ser Cys Leu Tyr Phe Ala Leu Ser Arg
                        180                 185                 190
        Tyr Leu Gly Phe Gly Arg Asp Ala Trp Val Tyr Pro Asp Pro Ala Gln
                        195                 200                 205
        Pro Gly Phe Glu Arg Leu Arg Arg Gln Tyr Leu Tyr Ser Phe Tyr Phe
                        210                 215                 220
        Ser Thr Leu Ile Leu Thr Thr Val Gly Asp Thr Pro Pro Ala Arg
        225                 230                 235                 240
        Glu Glu Glu Tyr Leu Phe Met Val Gly Asp Phe Leu Leu Ala Val Met
                        245                 250                 255
        Gly Phe Ala Thr Ile Met Gly Ser Met Ser Ser Val Ile Tyr Asn Met
                        260                 265                 270
        Asn Thr Ala Asp Ala Ala Phe Tyr Pro Asp His Ala Leu Val Lys Lys
                        275                 280                 285
        Tyr Met Lys Leu Gln His Val Asn Arg Lys Leu Glu Arg Arg Val Ile
                        290                 295                 300
        Asp Trp Tyr Gln His Leu Gln Ile Asn Lys Lys Met Thr Asn Glu Val
        305                 310                 315                 320
        Ala Ile Leu Gln His Leu Pro Glu Arg Leu Arg Ala Glu Val Ala Val
                        325                 330                 335
        Ser Val His Leu Ser Thr Leu Ser Arg Val Gln Ile Phe Gln Asn Cys
                        340                 345                 350
        Glu Ala Ser Leu Leu Glu Glu Leu Val Leu Lys Leu Gln Pro Gln Thr
                        355                 360                 365
        Tyr Ser Pro Gly Glu Tyr Val Cys Arg Lys Gly Asp Ile Gly Gln Glu
                        370                 375                 380
        Met Tyr Ile Ile Arg Glu Gly Gln Leu Ala Val Val Ala Asp Asp Gly
        385                 390                 395                 400
        Ile Thr Gln Tyr Ala Val Leu Gly Ala Gly Leu Tyr Phe Gly Glu Ile
                        405                 410                 415
        Ser Ile Ile Asn Ile Lys Gly Asn Met Ser Gly Asn Arg Arg Thr Ala
                        420                 425                 430
        Asn Ile Lys Ser Leu Gly Tyr Ser Asp Leu Phe Cys Leu Ser Lys Glu
                        435                 440                 445
        Asp Leu Arg Glu Val Leu Ser Glu Tyr Pro Gln Ala Gln Thr Ile Met
                        450                 455                 460
        Glu Glu Lys Gly Arg Glu Ile Leu Leu Lys Met Asn Lys Leu Asp Val
        465                 470                 475                 480
        Asn Ala Glu Ala Ala Glu Ile Ala Leu Gln Glu Ala Thr Glu Ser Arg
                        485                 490                 495
        Leu Arg Gly Leu Asp Gln Gln Leu Asp Asp Leu Gln Thr Lys Phe Ala
                        500                 505                 510
        Arg Leu Leu Ala Glu Leu Glu Ser Ser Ala Leu Lys Ile Ala Tyr Arg
                        515                 520                 525
        Ile Glu Arg Leu Glu Trp Gln Thr Arg Glu Trp Pro Met Pro Glu Asp
                        530                 535                 540
        Leu Ala Glu Ala Asp Asp Glu Gly Glu Pro Glu Gly Thr Ser Lys
        545                 550                 555                 560
        Asp Glu Glu Gly Arg Ala Ser Gln Glu Gly Pro Pro Gly Pro Glu
                        565                 570                 575
```

-continued

<210> SEQ ID NO 2
<211> LENGTH: 2308
<212> TYPE: DNA
<213> ORGANISM: Homo sapiens
<220> FEATURE:
<223> OTHER INFORMATION: cyclic nucleotide-gated cation channel 2B
      (CNG2B) complete nucleotide sequence derived from assembly of PCR
      fragments
<221> NAME/KEY: CDS
<222> LOCATION: (333)..(2060)
<223> OTHER INFORMATION: CNG2B

<400> SEQUENCE: 2

| | | | | | |
|---|---|---|---|---|---|
| agagggagg | aggaaaacag | agacaagact | caggcttccc | tctgaggcat | gcaccccac | 60 |
| cttctccagg | gatctcatta | gaggtgttta | gctgggcagg | tgtaagccca | ggccctggga | 120 |
| gacagggcag | agtgctagag | ctagactgtc | tccaccccct | cagtagcgct | agctctggtt | 180 |
| gtgttgctaa | gagccccaaa | gacaaagaag | tcacagcaga | agcccaacag | cagcctcctt | 240 |
| cagacagtca | ggcactagtg | cccaactcca | gaagtcccct | acaggcagag | agggtgtgga | 300 |
| catctcacac | cccagcacca | gaccacagaa | ccatgagcca | ggacaccaaa | gtgaagacaa | 360 |
| cagagtccag | tcccccagcc | ccatccaagg | ccaggaagtt | gctgcctgtc | ctggacccat | 420 |
| ctggggatta | ctactactgg | tggctgaaca | caatggtctt | cccagtcatg | tataacctca | 480 |
| tcatcctcgt | gtgcagagcc | tgcttccccg | acttgcagca | cggttatctg | tggcctggt | 540 |
| tggtgctgga | ctacacgagt | gacctgctat | acctactaga | catggtggtg | cgcttccaca | 600 |
| caggattctt | ggaacagggc | atcctggtgg | tggacaaggg | taggatctcg | agtcgctacg | 660 |
| ttcgcacctg | gagtttcttc | ttggacctgg | cttccctgat | gcccacagat | gtggtctacg | 720 |
| tgcggctggg | cccgcacaca | cccacccctga | ggctgaaccg | ctttctccgc | gcgccccgcc | 780 |
| tcttcgaggc | cttcgaccgc | acagagaccc | gcacagctta | cccaaatgcc | tttcgcattg | 840 |
| ccaagctgat | gctttacatt | tttgtcgtca | tccattggaa | cagctgccta | tactttgccc | 900 |
| tatcccggta | cctgggcttc | gggcgtgacg | catgggtgta | cccggacccc | gcgcagcctg | 960 |
| gctttgagcg | cctgcggcgc | cagtacctct | atagctttta | cttctccacg | ctgatactga | 1020 |
| ctacagtggg | cgatacaccg | ccgccagcca | gggaagaaga | gtacctcttc | atggtgggcg | 1080 |
| acttcctgct | ggccgtcatg | ggtttcgcca | ccatcatggg | tagcatgagc | tctgtcatct | 1140 |
| acaacatgaa | cactgcagat | gcggctttct | acccagatca | tgcactggtg | aagaagtaca | 1200 |
| tgaagctgca | gcacgtcaac | cgcaagctgg | agcggcgagt | tattgactgg | tatcagcacc | 1260 |
| tgcagatcaa | caagaagatg | accaacgagg | tagccatctt | acagcacttg | cctgagcggc | 1320 |
| tgcgggcaga | agtggctgtg | tctgtgcacc | tgtccactct | gagccgggtg | cagatctttc | 1380 |
| agaactgtga | ggccagcctg | ctggaggagc | tggtgctgaa | gctgcagccc | cagacctact | 1440 |
| caccaggtga | atatgtatgc | cgcaaaggag | acattggcca | agagatgtac | atcatccgag | 1500 |
| agggtcaact | ggccgtggtg | gcagatgatg | gtatcacaca | gtatgctgtg | ctcggtgcag | 1560 |
| ggctctactt | tgggggagatc | agcatcatca | acatcaaagg | gaacatgtct | gggaaccgcc | 1620 |
| gcacagccaa | catcaagagc | ctaggttatt | cagacctatt | ctgcctgagc | aaggaggacc | 1680 |
| tgcgggaggt | gctgagcgag | tatccacaag | cacagaccat | catggaggag | aaaggacgtg | 1740 |
| agatcctgct | gaaaatgaac | aagttggacg | tgaatgctga | ggcagctgag | atcgccctgc | 1800 |
| aggaggccac | agagtcccgg | ctacgaggcc | tagaccagca | gctggatgat | ctacagacca | 1860 |
| agtttgctcg | cctcctggct | gagctggagt | ccagcgcact | taagattgct | taccgcattg | 1920 |

| | |
|---|---|
| aacggctgga gtggcagact cgagagtggc caatgcccga ggacctggct gaggctgatg | 1980 |
| acgagggtga gcctgaggag ggaacttcca aagatgaaga gggcagggcc agccaggagg | 2040 |
| gacccccagg tccagagtga ccccatcccc atccccagga ttccacctc ctagtgaatc | 2100 |
| cagagttgta gtaaagccta actgctgcaa ctctgtcatc ctgtctgcga gatcacagac | 2160 |
| acaggagcga attggtctgt agatgcccag ctagagatat aggagtttaa cgcacattca | 2220 |
| gccccactt accagtacac acacacacac acacacacac acatttgctc atagacctgt | 2280 |
| tggccccaag actgtgcatt ccatctaa | 2308 |

```
<210> SEQ ID NO 3
<211> LENGTH: 1728
<212> TYPE: DNA
<213> ORGANISM: Homo sapiens
<220> FEATURE:
<223> OTHER INFORMATION: cyclic nucleotide-gated cation channel 2B
      (CNG2B) coding sequence
<221> NAME/KEY: CDS
<222> LOCATION: (1)..(1728)
<223> OTHER INFORMATION: CNG2B

<400> SEQUENCE: 3
```

| | |
|---|---|
| atgagccagg acaccaaagt gaagacaaca gagtccagtc ccccagcccc atccaaggcc | 60 |
| aggaagttgc tgcctgtcct ggacccatct ggggattact actactggtg gctgaacaca | 120 |
| atggtcttcc cagtcatgta aacctcatc atcctcgtgt gcagagcctg cttccccgac | 180 |
| ttgcagcacg gttatctggt ggcctggttg gtgctggact acacgagtga cctgctatac | 240 |
| ctactagaca tggtggtgcg cttccacaca ggattcttgg aacagggcat cctggtggtg | 300 |
| gacaagggta ggatctcgag tcgctacgtt cgcacctgga gtttcttctt ggacctggct | 360 |
| tccctgatgc ccacagatgt ggtctacgtg cggctgggcc cgcacacacc caccctgagg | 420 |
| ctgaaccgct ttctccgcgc gccccgcctc ttcgaggcct cgaccgcac agagacccgc | 480 |
| acagcttacc caaatgcctt tcgcattgcc aagctgatgc tttacatttt tgtcgtcatc | 540 |
| cattggaaca gctgcctata ctttgcccta tcccggtacc tgggcttcgg gcgtgacgca | 600 |
| tgggtgtacc cggaccccgc gcagcctggc tttgagcgcc tgcggcgcca gtacctctat | 660 |
| agcttttact tctccacgct gatactgact acagtgggcg atacaccgcc gccagccagg | 720 |
| gaagaagagt acctcttcat ggtgggcgac ttcctgctgg ccgtcatggg tttcgccacc | 780 |
| atcatgggta gcatgagctc tgtcatctac aacatgaaca ctgcagatgc ggcttctac | 840 |
| ccagatcatg cactggtgaa gaagtacatg aagctgcagc acgtcaaccg caagctggag | 900 |
| cggcgagtta ttgactggta tcagcacctg cagatcaaca gaagatgac caacgaggta | 960 |
| gccatcttac agcacttgcc tgagcggctg cgggcagaag tggctgtgtc tgtgcacctg | 1020 |
| tccactctga gccgggtgca gatctttcag aactgtgagg ccagcctgct ggaggagctg | 1080 |
| gtgctgaagc tgcagcccca gacctactca ccaggtgaat atgtatgccg caaggagac | 1140 |
| attggccaag agatgtacat catccgagag ggtcaactgg ccgtggtggc agatgatggt | 1200 |
| atcacacagt atgctgtgct cggtgcaggg ctctactttg gggagatcag catcatcaac | 1260 |
| atcaaaggga acatgtctgg aaccgccgc acagccaaca tcaagagcct aggttattca | 1320 |
| gacctattct gcctgagcaa ggaggacctg cgggaggtgc tgagcgagta tccacaagca | 1380 |
| cagaccatca tggaggagaa aggacgtgag atcctgctga aaatgaacaa gttggacgtg | 1440 |
| aatgctgagg cagctgagat cgccctgcag gaggccacag agtcccggct acgaggccta | 1500 |

-continued

```
gaccagcagc tggatgatct acagaccaag tttgctcgcc tcctggctga gctggagtcc    1560
agcgcactta agattgctta ccgcattgaa cggctggagt ggcagactcg agagtggcca    1620
atgcccgagg acctggctga ggctgatgac gagggtgagc ctgaggaggg aacttccaaa    1680
gatgaagagg gcagggccag ccaggaggga cccccaggtc cagagtga                1728
```

```
<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:sense strand
      amplification primer Oligo 1

<400> SEQUENCE: 4
gcagatcttt cagaactgtg aggcca                                          26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:antisense
      strand amplification primer Oligo 2

<400> SEQUENCE: 5
cctgccctct tcatctttgg aagttc                                          26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:sense strand
      first round 3' RACE gene-specific amplification primer Oligo 3

<400> SEQUENCE: 6
gccaacatca agagcctagg ttattc                                          26

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:sense strand
      nested gene specific amplification primer Oligo 4

<400> SEQUENCE: 7
ggatgatcta cagaccaagt ttgctcg                                         27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:sense strand
      primer

<400> SEQUENCE: 8
atgagccagg acaccaaagt gaagac                                          26

<210> SEQ ID NO 9
<211> LENGTH: 25
<212> TYPE: DNA
<213> ORGANISM: Artificial Sequence
<220> FEATURE:
```

```
<223> OTHER INFORMATION: Description of Artificial Sequence:antisense
      strand primer Oligo 6 specific to human CNG2B

<400> SEQUENCE: 9
gttgatgatg ctgatctccc caaag                                          25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:CNG2B-
      specific antisense strand first round 5' RACE PCR primer Oligo 7

<400> SEQUENCE: 10
ggatgatgag gttatacatg actggg                                         26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:antisense
      strand nested CNG2B specific amplification primer Oligo 8

<400> SEQUENCE: 11
aggctagcaa cttcctggcc ttggat                                         26

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:sense strand
      primer Oligo 9

<400> SEQUENCE: 12
gcgaaagctt ccaccatgag ccaggacacc aaagtg                              36

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:antisense
      strand primer Oligo 10

<400> SEQUENCE: 13
catgtctaga atggggatgg ggtcactctg gacct                               35

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:sense strand
      amplification primer Oligo 1

<400> SEQUENCE: 14
gcagatcttc cagaactgta aggcca                                         26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:degenerate
``` sense strand primer Oligo 5 based on N-terminal amino acid
sequence or rat OCNC2
<221> NAME/KEY: modified_base
<222> LOCATION: (1)..(26)
<223> OTHER INFORMATION: n = g, a, c or t

<400> SEQUENCE: 15
atgagccagg acggnaargt naarac                                      26

<210> SEQ ID NO 16
<211> LENGTH: 575
<212> TYPE: PRT
<213> ORGANISM: Rattus norvegicus
<220> FEATURE:
<223> OTHER INFORMATION: rat cyclic nucleotide gated cation channel
      OCNC2

<400> SEQUENCE: 16

Met Ser Gln Asp Gly Lys Val Lys Thr Thr Glu Ser Thr Pro Pro Ala
 1               5                  10                  15

Pro Thr Lys Ala Arg Lys Trp Leu Pro Val Leu Asp Pro Ser Gly Asp
            20                  25                  30

Tyr Tyr Tyr Trp Trp Leu Asn Thr Met Val Phe Pro Ile Met Tyr Asn
        35                  40                  45

Leu Ile Ile Val Val Cys Arg Ala Cys Phe Pro Asp Leu Gln His Ser
    50                  55                  60

Tyr Leu Val Ala Trp Phe Val Leu Asp Tyr Thr Ser Asp Leu Leu Tyr
65                  70                  75                  80

Leu Leu Asp Ile Gly Val Arg Phe His Thr Gly Phe Leu Glu Gln Gly
                85                  90                  95

Ile Leu Val Val Asp Lys Gly Met Ile Ala Ser Arg Tyr Val Arg Thr
            100                 105                 110

Trp Ser Phe Leu Leu Asp Leu Ala Ser Leu Val Pro Thr Asp Ala Ala
        115                 120                 125

Tyr Val Gln Leu Gly Pro His Ile Pro Thr Leu Arg Leu Asn Arg Phe
    130                 135                 140

Leu Arg Val Pro Arg Leu Phe Glu Ala Phe Asp Arg Thr Glu Thr Arg
145                 150                 155                 160

Thr Ala Tyr Pro Asn Ala Phe Arg Ile Ala Lys Leu Met Leu Tyr Ile
                165                 170                 175

Phe Val Val Ile His Trp Asn Ser Cys Leu Tyr Phe Ala Leu Ser Arg
            180                 185                 190

Tyr Leu Gly Phe Gly Arg Asp Ala Trp Val Tyr Pro Asp Pro Ala Gln
        195                 200                 205

Pro Gly Phe Glu Arg Leu Arg Arg Gln Tyr Leu Tyr Ser Phe Tyr Phe
    210                 215                 220

Ser Thr Leu Ile Leu Thr Thr Val Gly Asp Thr Pro Leu Pro Asp Arg
225                 230                 235                 240

Glu Glu Glu Tyr Leu Phe Met Val Gly Asp Phe Leu Leu Ala Val Met
                245                 250                 255

Gly Phe Ala Thr Ile Met Gly Ser Met Ser Ser Val Ile Tyr Asn Met
            260                 265                 270

Asn Thr Ala Asp Ala Ala Phe Tyr Pro Asp His Ala Leu Val Lys Lys
        275                 280                 285

Tyr Met Lys Leu Gln His Val Asn Lys Arg Leu Glu Arg Arg Val Ile
    290                 295                 300

Asp Trp Tyr Gln His Leu Gln Ile Asn Lys Lys Met Thr Asn Glu Val

-continued

```
305                 310                 315                 320
Ala Ile Leu Gln His Leu Pro Glu Arg Leu Arg Ala Glu Val Ala Val
                325                 330                 335
Ser Val His Leu Ser Thr Leu Ser Arg Val Gln Ile Phe Gln Asn Cys
                340                 345                 350
Glu Ala Ser Leu Leu Glu Glu Leu Val Leu Lys Leu Gln Pro Gln Thr
                355                 360                 365
Tyr Ser Pro Gly Glu Tyr Val Cys Arg Lys Gly Asp Ile Gly Arg Glu
                370             375                 380
Met Tyr Ile Ile Arg Glu Gly Gln Leu Ala Val Val Ala Asp Asp Gly
385                 390                 395                 400
Val Thr Gln Tyr Ala Val Leu Gly Ala Gly Leu Tyr Phe Gly Glu Ile
                405                 410                 415
Ser Ile Ile Asn Ile Lys Gly Asn Met Ser Gly Asn Arg Arg Thr Ala
                420                 425                 430
Asn Ile Lys Ser Leu Gly Tyr Ser Asp Leu Phe Cys Leu Ser Lys Glu
                435                 440                 445
Asp Leu Arg Glu Val Leu Ser Glu Tyr Pro Gln Ala Gln Ala Val Met
    450                 455                 460
Glu Glu Lys Gly Arg Glu Ile Leu Leu Lys Met Asn Lys Leu Asp Val
465                 470                 475                 480
Asn Ala Glu Ala Ala Glu Ile Ala Leu Gln Glu Ala Thr Glu Ser Arg
                485                 490                 495
Leu Lys Gly Leu Asp Gln Gln Leu Asp Asp Leu Gln Thr Lys Phe Ala
                500                 505                 510
Arg Leu Leu Ala Glu Leu Glu Ser Ser Ala Leu Lys Ile Ala Tyr Arg
                515                 520                 525
Ile Glu Arg Leu Glu Trp Gln Thr Arg Glu Trp Pro Met Pro Glu Asp
    530                 535                 540
Met Gly Glu Ala Asp Asp Glu Ala Glu Pro Gly Glu Gly Thr Ser Lys
545                 550                 555                 560
Asp Gly Glu Gly Lys Ala Gly Gln Ala Gly Pro Ser Gly Ile Glu
                565                 570                 575
```